US00PP32821P2

(12) United States Plant Patent
Meilland

(10) Patent No.: US PP32,821 P2
(45) Date of Patent: Feb. 23, 2021

(54) BEDDING ROSE PLANT NAMED 'MEITULACA'

(50) Latin Name: *Rosa hybrida*
Varietal Denomination: MEITULACA

(71) Applicant: The Conard-Pyle Company, West Grove, PA (US)

(72) Inventor: Alain Antoine Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/602,662

(22) Filed: Nov. 19, 2019

(51) Int. Cl.
*A01H 5/02* (2018.01)
*A01H 6/74* (2018.01)

(52) U.S. Cl.
USPC ..... Plt./125

(58) Field of Classification Search
USPC ..... Plt./101, 123, 125
See application file for complete search history.

(56) References Cited

U.S. PATENT DOCUMENTS

PP26,790 P3 6/2016 Meilland et al.

*Primary Examiner* — Susan McCormick Ewoldt
*Assistant Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of rose plant, herein referred to by its cultivar name, 'MEITULACA', is provided which displays an exceptional and nearly continuous blooming of attractive, cup shaped yellow-white colored flowers. Attractive very dense foliage with a glossy aspect is formed, which contrasts beautifully with the blossoms. A bushy growth habit is displayed. The new variety is well suited for proving attractive ornamentation in the landscape.

1 Drawing Sheet

Botanical/commercial classification:
Latin name: *Rosa hybrida.*
Varietal denomination: 'MEITULACA'.

SUMMARY OF THE INVENTION

The new variety of *Rosa hybrida* rose plant was created by artificial pollination wherein two parents were crossed which previously had been studied in the hope that they would contribute the desired characteristics. The female parent (i.e., the seed parent) was the 'BLUSH NOISETTE' variety (not patented). The male parent (i.e., the pollen parent) was the 'MEITUNE' variety (not patented).

The parentage of the new variety can be summarized as follows:

'BLUSH NOISETTE' x 'MEITUNE'

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms attractive, cup shaped, yellow-white colored flowers,
(b) exhibits very dense, glossy foliage,
(c) displays a bushy growth habit, and
(d) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'BLUSH NOISETTE' variety (i.e., the seed parent) displays approximately 35 petals on average, which is less than the new variety and the 'MEITUNE' variety (i.e., the pollen parent) displays light pink colored flowers, whereas the new variety displays yellow-white colored flowers. Moreover, the new variety can be readily distinguished from related similar non-parental varieties. For example, the 'Meiradena' variety (U.S. Plant Pat. No. 26,790) displays less petals compared to the new variety.

The new variety has been found to undergo asexual propagation in Le Cannet des Maures, Var, France by a number of routes, including budding, grafting, and the use of cuttings. Asexual propagation by the above-mentioned techniques in Le Cannet des Maures, Var, France has shown that the characteristics of the new variety are stable and are strictly transmissible by such asexual propagation from one generation to another. Accordingly, the new variety undergoes asexual propagation in a true-to-type manner.

The new variety has been named 'MEITULACA'.

BRIEF DESCRIPTION OF THE PHOTOGRAPH

The accompanying photograph of FIG. 1 shows as nearly true as it is reasonably possible to make the same, in a color illustration of this character, typical specimens of the plant parts of the new variety. The rose plants of the new variety were approximately two years of age and were observed during June while budded on their own roots and growing outdoors at Le Cannet des Maures, Var, France. Dimensions in centimeters are indicated at the bottom of FIG. 1.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—reverse.

Element 7—illustrates a specimen of an open flower—plan view—obverse.

Element 8—illustrates a specimen of a fully open flower—plan view—reverse.

Element 9—illustrates a specimen of a fully open flower—plan view—obverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 7 leaflets—plan view—upper surface.

Element 15—illustrates a specimen of a leaf with 5 leaflets—plan view—upper surface.

Element 16—illustrates a specimen of a leaf with 3 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of two-year-old specimens of the new variety during July while budded on their own roots and growing outdoors at Le Cannet des Maures, Var, France.

Plant:

*Commercial classification.*—Shrub.

*Habit.*—Bushy.

*Height.*—Near 65 to 80 cm on average.

*Width.*—Near 70 cm on average.

Branches:

*Color.*—Young stems: commonly near Yellow-Green Group 146C. Adult wood: commonly near Yellow-Green Group 146C.

*Length.*—Main stems: near 40 to 70 cm on average. Secondary stems: near 10 to 25 cm on average.

*Diameter.*—Typically between 0.3 to 0.9 cm.

*Internode length.*—Typically between 3.0 to 7.0 cm.

*Thorns.*—Configuration on adult stems: slightly elongated on the upper surface and slightly concave on the under surface. Long prickles — quantity: commonly 1 thorn per 10 cm long young stem and commonly 5 thorns per 10 cm long adult stem. Long prickles — base shape: oval. Long prickles — length: commonly near 0.4 cm on average on young stems and commonly near 1.3 cm on average on adult stems. Long prickles — color: commonly near Yellow-Green Group 144D on young stems and commonly between near Greyed-Orange Group 166B and near Greyed-Orange Group 166A on adult stems. Small prickles: none observed.

Foliage:

*General appearance.*—Very dense with a glossy aspect.

*Number of leaflets.*—3, 5, and 7; most often 5 and 7.

*New foliage.*—Upper surface color: commonly near Green Group 137C. Under surface color: commonly near Green Group 138B.

*Adult foliage.*—Upper surface color: commonly near Green Group 137A. Under surface color: commonly near Green Group 137D.

*Entire leaf.*—Length: typically between 8.0 to 13.0 cm. Width: typically between 6.0 to 8.0 cm.

Leaflets:

*Shape.*—Tip: cuspidate. Base: obtuse.

*Texture.*—Leathery.

*General appearance.*—Oval.

*Edge.*—Slightly denticulate.

*Serration.*—Small and single.

*Terminal leaflet.*—Length: approximately 6.0 cm on average. Width: approximately 3.7 cm on average.

*Petiole rachis.*—Color of upper surface: commonly near Yellow-Green Group 146B. Color of under surface: commonly near Yellow-Green Group 146C. Length: typically between 3.0 to 6.5 cm. Width: typically between 0.1 to 0.15 cm.

*Petioles.*—Upper surface: no glandular. Under surface: no prickles. Color of upper surface: commonly near Yellow-Green Group 146B. Color of under surface: commonly near Yellow-Green Group 146C. Petiole length of terminal leaflet: approximately 1.8 cm on average. Petiole diameter of terminal leaflet: approximately 0.1 cm on average.

*Stipules.*—General appearance: adnate, pectinate and rather broad. Length: approximately 1.4 cm on average. Width: approximately 0.5 cm on average. Color of upper surface: commonly near Yellow-Green Group 148B. Color of under surface: commonly between near Yellow-Green Group 148B and Yellow-Green Group 148C.

Inflorescence:

*Number of flowers per stem.*—Generally between 3 to 12 flowers per stem.

*Lastingness of the bloom.*—Commonly between 3 to 5 days.

*Bud.*—Shape: conical. Size: medium. Length: approximately 1.1 cm on average. Width: approximately 1.0 cm on average. Color as calyx breaks: upper surface: commonly near White Group 155C suffused with near Green-White Group 157D. under surface: commonly near White Group 155C suffused with near Green White Group 157D.

*Sepals.*—Length: approximately 2.0 cm on average. Width: approximately near 0.6 cm on average. Shape: without extension; at the top: longish, at the base: upright. Margin: haily with 0 to 3 extensions, in which extension length is approximately 5 mm on average and extension width is approximately 0.1 mm on average. Upper surface: texture: tomentous. color: commonly near Yellow-Green Group 148C. Under surface: texture: smooth. color: commonly near Yellow-Green Group 147C.

*Receptacle*.—Color: commonly near Yellow-Green Group 147C. Length: approximately 0.4 cm on average. Width: approximately 0.4 cm on average. Surface: smooth. Shape: funnel shaped.

*Peduncle*.—Length: approximately 3.5 cm on average. Width: approximately 0.2 cm on average. Surface: pubescent. Color: commonly near Yellow-Green Group 147C.

*Flower*.—Average diameter when open: commonly between near 6.0 to 7.0 cm on average. Average depth when open: approximately 2.5 to 3.0 cm on average. Shape: cup shaped. Number of petals under normal conditions: approximately 57 to 66 petals on average. Shape of the petal: base: obtuse. top: rounded. Texture of the petal: leathery. Petal length: approximately 2.0 cm on average. Petal width: approximately 1.7 cm on average. Petal arrangement: imbricated. Petal drop: petals drop off cleanly before drying. Fragrance: none. Color when opening: upper surface: commonly near Yellow-White Group 158C. under surface: commonly near Yellow-White Group 158C. Color of the open flower: upper surface: commonly near Yellow-White Group 158C. under surface: commonly near Yellow-White Group 158C. Petaloids: number is approximately 5 per flower; length is typically between 0.3 to 1.0 cm; width is typically between 0.2 to 0.8 cm; color is commonly near Yellow-White Group 158C.

*Reproductive parts*.—Anthers: number is approximately 39 on average, length is approximately 0.1 cm on average, coloration is commonly near Yellow-Orange Group 17D, and arrangement is regular around styles. Filaments: length is approximately 0.2 cm on average and coloration is commonly near Yellow Group 2D. Styles: length is approximately 0.2 cm on average, coloration is commonly near Yellow Group 2D, and number is approximately 46 on average. Stigmas: size is approximately 0.2 cm on average and coloration is commonly near Red Group 42A. Pollen: not available at this stage. Hips: not available at this stage.

Development:

*Vegetation*.—Strong.

*Blooming*.—Early in the season, very abundant and nearly continuous, typically from May to October in Le Cannet des Maures, Var, France.

*USDA hardiness zone*.—Zone 5.

*Tolerance to disease*.—Very good, particularly against black spot (*Diplocarpon rosae*).

The new 'MEITULACA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant characterized by the following combination of characteristics:

(a) forms attractive, cup shaped, yellow-white colored flowers, (b) exhibits very dense, glossy foliage, (c) displays a bushy growth habit, and (d) is well suited for providing attractive ornamentation; substantially as herein shown and described.

* * * * *

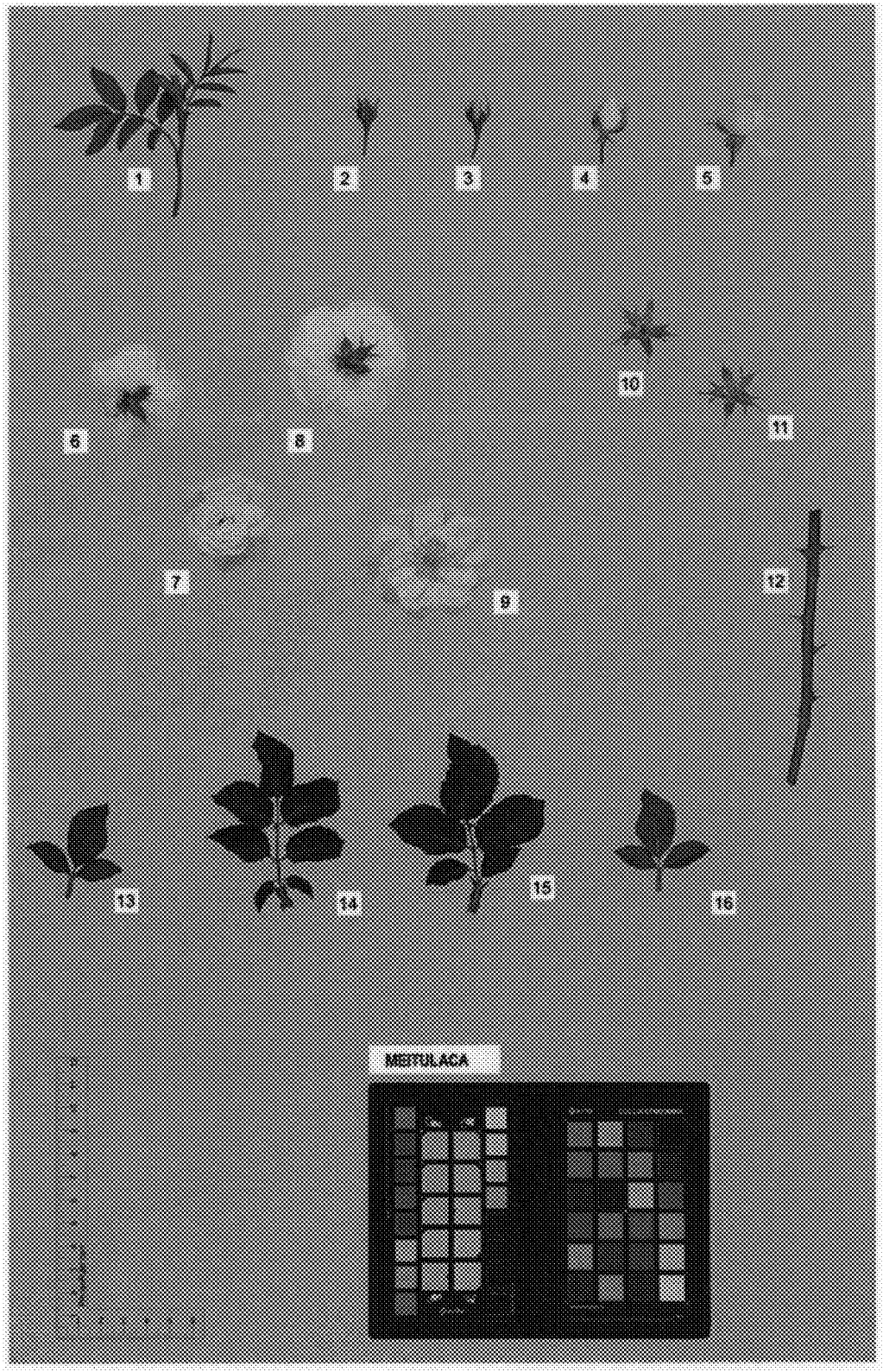
1
2
3
4
5
6
8
10
11
7
9
12
13
14
15
16
METTULACA